United States Patent [19]

Sacco

[11] Patent Number: 5,061,248
[45] Date of Patent: Oct. 29, 1991

[54] INJECTION PORT SAFETY SHIELD

[76] Inventor: John J. Sacco, 202 Sedgwick Dr., Syracuse, N.Y. 13203

[21] Appl. No.: 503,938

[22] Filed: Apr. 4, 1990

[51] Int. Cl.⁵ .............................................. A61M 5/32
[52] U.S. Cl. ..................................... 604/192; 604/86; 604/263
[58] Field of Search .................. 604/83, 86, 192, 283, 604/263, 82, 87, 88

[56] References Cited

U.S. PATENT DOCUMENTS 4,723,948  2/1988  Clark et al. ........................ 604/283
4,878,897 11/1989  Katzin ................................. 604/86
4,921,489  5/1990  Frizzell .............................. 604/192
4,946,445  8/1990  Lynn .................................. 604/192
4,966,582 10/1990  Sit et al. ............................. 604/86
4,986,817  1/1991  Code .................................. 604/192

*Primary Examiner*—John D. Yasko
*Assistant Examiner*—Adam J. Cermak
*Attorney, Agent, or Firm*—Wall and Roehrig

[57] ABSTRACT

A needle shield that can be clamped about the line of a flow path used to administer IV fluids to a patient immediately beneath an insertion port to protect a health care worker from receiving acccidental needle wounds.

12 Claims, 1 Drawing Sheet

INJECTION PORT SAFETY SHIELD

BACKGROUND OF THE INVENTION

This invention relates to a hand shield for use in association with an injection port of an intravenous flow path to prevent accidental puncture wounds from occurring.

Flow paths for gravity feeding IV solutions to a patient are generally equipped with an injection port through which blood and/or medications can be delivered directly into the flow line for rapid administration. The injection port typically includes a short piece of tubing that enters the main flow line at an angle and is capped at its distal end by a needle penetratable membrane. It is not uncommon for a health care worker who is attempting to insert a needle into the port to have the needle slip and puncture the hand that is used to steady the port. Accidental needlesticks are not potentially dangerous in themselves but they do provide openings in the skin through which infections such as AIDS, hepatitis or the like can be acquired.

SUMMARY OF THE INVENTION

It is therefore an object of the present invention to provide for the safety of health care workers.

A further object of the present invention is to provide a safety shield that can be mounted in a flow path directly beneath an injection port which will help prevent accidental needle wounds.

Another object of the present invention is to provide an injection port shield that can be removably secured to a flow path used to administer intravenous fluids.

Yet another object of the present invention is to provide a two-piece shield that can be adjustably clamped about an IV flow line beneath an injection port for protecting the hand of a health care worker holding the line during an injection procedure.

These and other objects of the present invention are attained by means of an injection port shield that includes a radially-expanded flange that is mounted upon an axially-disposed hub. The hub and the flange are divided into two half-sections along a parting line and are hinged so they can move between an open and a closed position. A hole passes axially through the shield and permits the sections to be closed securely over a flow line adjacent to an injection port to form a guard for protecting the hand of a health care worker who is holding the line steady during an injection procedure. The shield is further equipped with an adjustable clasp which allows the two half-sections to be secured against the flow line without crimping or damaging the line.

BRIEF DESCRIPTION OF THE DRAWINGS

For a better understanding of these and other objects of the present invention reference will be made to the following detailed description of the invention which is to be read in association with the accompanying drawings wherein.

DESCRIPTION OF THE INVENTION

Figure 1:
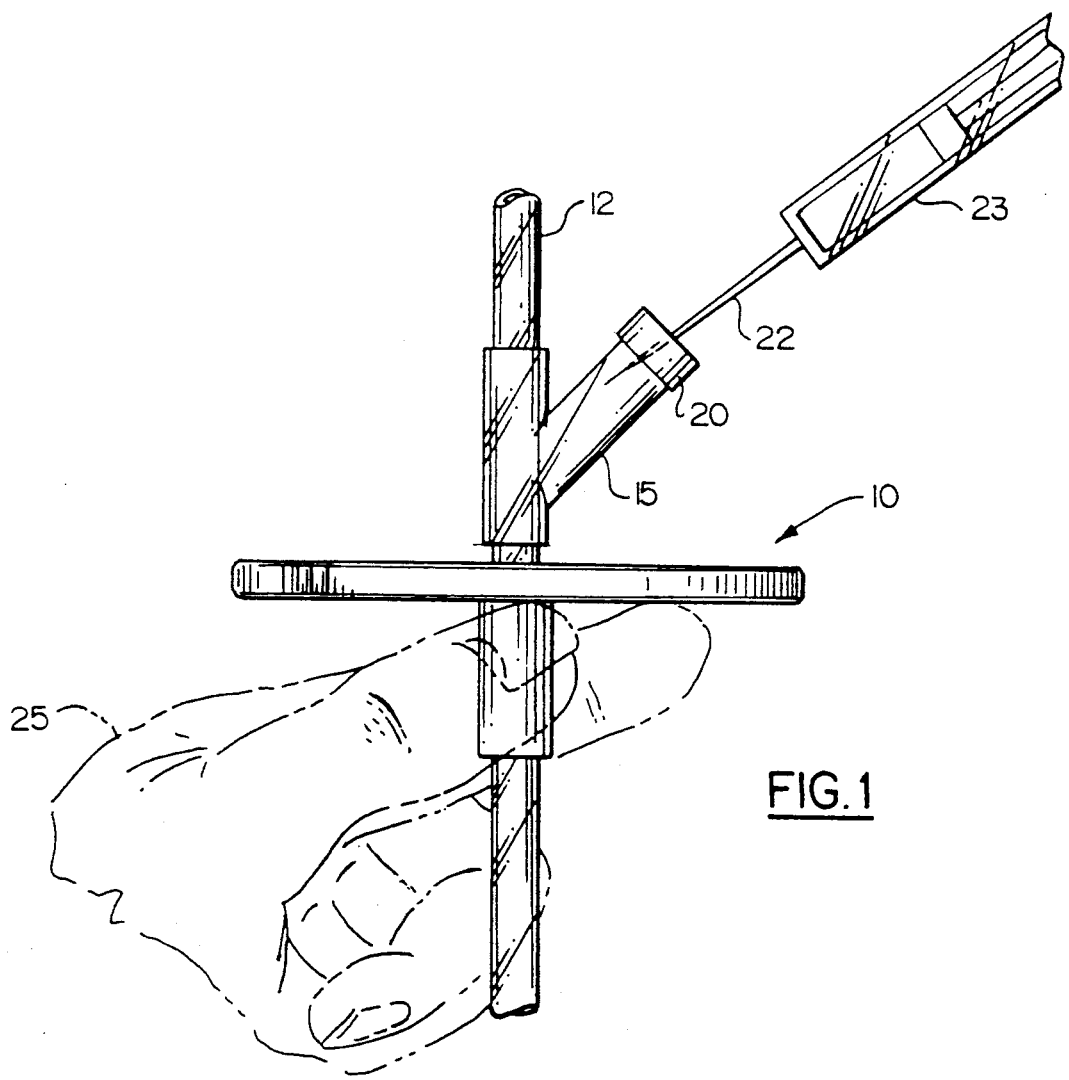
FIG. 1 is a side elevation of a shield embodying the teachings of the present invention.

Turning now to the drawings, there is shown a needle shield, generally referenced 10, that can be mounted on the flow line of an IV set for administering fluids intravenously. The flow line is made of flexible clear plastic tubing 12 and is equipped with an injection port to allow for more rapid infusion of medication or the like. The injection port is a Y-shaped connector 13 that is mounted at a desired location in the flow line close enough to the lower or infusion end of the line to enable the fluid injection through the port to be rapidly administered. The injection port includes an upwardly raised arm 15 that extends radially from the main leg 17 of the connector a sufficient distance to provide ready access to a needle. The distal end of the arm 15 is capped with a needle penetratable membrane 20 which can be formed of rubber or any other suitable material that is known and used in the art.

In this embodiment of the invention, the membrane is shown being penetrated by the needle 22 of a syringe 23 to deliver a desired medication directly into the flow line. As shown in FIG. 1, during the injection procedure, the health care worker uses one hand 25 to hold and steady the flow line beneath the injection port and the other to insert the needle in the port and complete the administration procedure. A needle that does not find the port during insertion can slip downwardly and puncture the skin of the hand holding the line thereby producing a potentially dangerous puncture wound.

Figure 2:
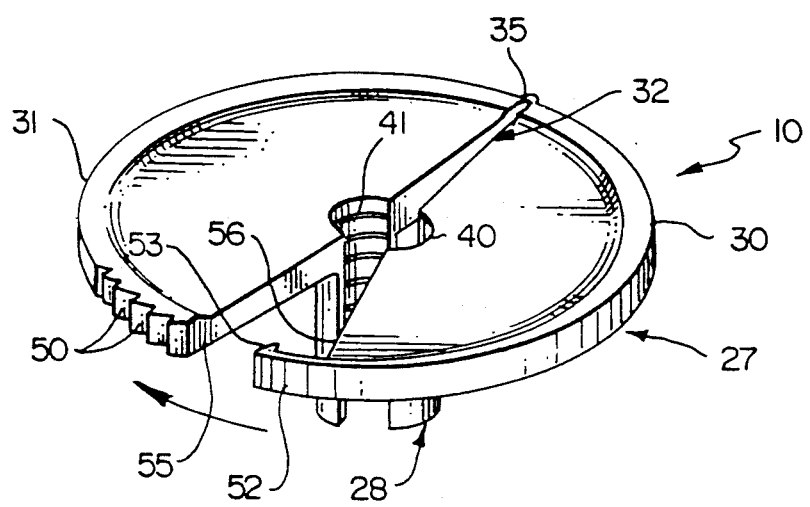
FIG. 2 is a perspective view showing the shield illustrated in FIG. 1 in an open position.

The shield of the present invention is designed to be placed about the flow line immediately below the injection port to protect the worker's hand. As best illustrated in FIG. 2, the shield 10 is generally circular in form and includes a radially-expanded upper flange 27 that is mounted on top of a cylindrical hub 28. The flange and hub are divided into two half-sections 30 and 31 along a parting line 32 that generally bisects the shield. The two half-sections are co-joined by means of a hinge 35 located along the outer perimeter of the flange. The half-sections and the hinge are preferably molded in one operation from a suitable plastic material. This type of hinge is sometimes referred to as a "living hinge".

An axially-disposed hole 40 is formed in the shield which is dimensioned to receive the main flow line therein. The inner wall surface of the hole is roughened or textured, as for example by means of raised ribs 41, which permits the shield to securely grasp the flow line tubing and prevent the shield from sliding along the line.

The outer periphery of the flange contains an upwardly raised rim 44 which is elevated sufficiently to contain the tip of a needle that might inadvertently strike the shield during an injection procedure.

A series of ratchet teeth 50-50 are molded along the perimeter of half-section 31 adjacent to the parting line 32. A flexible tab 52 is similarly molded in the opposite half-section 30. The tab extends outwardly from the edge of the section at the parting line toward the ratchet teeth carried by the other section. The distal end of the tab is equipped with an inwardly directed tooth 53 that is arranged to mesh with the ratchet teeth and thus form a clamp for holding the shield in a closed position about the flow line.

The end faces 55 and 56 of the half-sections defining the parting line are molded so that they form a slight angle at closure. This, in turn, allows sufficient clearance so that the half-sections can be tightened firmly about the flow line. This clearance is shown slightly exaggerated in FIG. 2 for explanatory purposes.

As should be evident from the disclosure above, the shield of the present invention can be conveniently slipped around the line of the flow path directly below an injection port and closed against the line using the clamp arrangement. The clamp arrangement permits the holding pressure exerted by the half-sections against the flow line to be adjusted so that the shield will not crimp or damage the line but yet prevent the shield from sliding along the line. The ribs 41 will bite gently into the line and thus help hold the shield in a desired position. The shield flange is sufficiently large so that it extends radially well beyond the distal end of the injection port arm to fully encompasses the worker's hand. As a result of this construction, a needle slipping out of the injection port will be prevented from striking the worker's hand and causing a potentially dangerous wound. It should also be further noted that the instant shield can be completely molded in one relatively simple operation thereby permitting the device to be manufactured at a comparatively low unit cost. The fabrication materials may be further selected from suitable plastics that can be thoroughly cleansed after use thereby enabling repeated use of the device.

While this invention has been described in the specification, and illustrated in the drawings, with reference to the preferred embodiment, it will be understood by those skilled in the art that various changes may be made and equivalents substituted without departing from the scope of the claims herein.

What is claimed is:

1. A shield for an injection port of a fluid path for administering fluids intravenously to a patient that includes
    an expanded flange mounted upon a hollow cylindrical hub that is dimensioned to surround an intravenous flow line, said flange and said hub being separated into two half-sections along a common parting line and a hole passing through said flange whereby the shield can be passed around the flow line immediately below an injection port,
    a hinge means for movably securing the two half-sections whereby the shield can be opened and closed about said flow line,
    adjustable clamp means for removably securing the two half-sections in a closed position about said flow line to lock the half-sections against the line and thus prevent the shield from sliding therealong.

2. The shield of claim 1 wherein the flange is circular in form.

3. The shield of claim 2 wherein the top surface of said flange includes a raised rim about its periphery.

4. The shield of claim 1 wherein the interior wall of said hole contains a plurality of raised ridges for locking against the outer surface of a flow line.

5. The shield of claim 1 wherein said flange and said hub of each half-section are molded as a single component and the two half-sections are joined by a molded hinge that is integral therewith.

6. The shield of claim 5 wherein said clamp means is adjustable and further includes a series of teeth molded along the periphery of one half-section adjacent said parting line and a strap molded in the other half-section having at least one tooth that mates with the teeth in the other half-section to secure the shield in a closed position.

7. The shield of claim 1 wherein the hub is an elongated tubular member that provides a positive hand hold to the user.

8. A shield for an injection port of a fluid path for administering fluids intravenously to a patient that includes:
    an expanded flange mounted on a hollow cylindrical hub that is dimensioned to surround an intravenous flow line, said flange and said hub being separated into two half-sections along a common parting line and a hole passing through said flange, whereby the shield can be passed around the flow line immediately below an injection port, said flange and said hub of each half-section being molded as a single component,
    a molded hinge integral with said flange and said hub for movably securing the two half-sections, whereby the shield can be opened and closed about said flow line, and
    a clamp means for securing the two half-sections in a closed position about the flow line to lock the half-sections against the line and thus prevent the shield from sliding therealong, said clamp means being adjustable and further including a series of teeth molded along the periphery of one half-section adjacent said parting line and a strap molded in the other half-section having at least one tooth that mates with the teeth in the other half-section to secure the shield in a closed position.

9. The shield of claim 8 wherein the flange is circular in form.

10. The shield of claim 9 wherein said flange has a top surface that includes a raised rim about its periphery.

11. The shield of claim 8 wherein said hole has an interior surface containing a plurality of raised ridges for locking against the outer surface of a flow line.

12. The shield of claim 8 wherein the hub is an elongated tubular member that provides a positive hand hold to the user.

* * * * *